US008290301B2

(12) United States Patent
Robinson

(10) Patent No.: US 8,290,301 B2
(45) Date of Patent: Oct. 16, 2012

(54) OPTIMIZED IMAGING SYSTEM FOR COLLECTION OF HIGH RESOLUTION IMAGERY

(75) Inventor: Ian S. Robinson, Redondo Beach, CA (US)

(73) Assignee: Raytheon Company, Waltham, MA (US)

(*) Notice: Subject to any disclaimer, the term of this patent is extended or adjusted under 35 U.S.C. 154(b) by 877 days.

(21) Appl. No.: 12/367,480

(22) Filed: Feb. 6, 2009

(65) Prior Publication Data
US 2010/0202683 A1    Aug. 12, 2010

(51) Int. Cl.
*G06K 9/36* (2006.01)
(52) U.S. Cl. ....... 382/284; 382/274; 382/275; 358/3.26; 358/3.27; 358/450
(58) Field of Classification Search .......... 382/274, 382/275, 282, 284
See application file for complete search history.

(56) References Cited

U.S. PATENT DOCUMENTS

| | | | |
|---|---|---|---|
| 6,011,875 A | 1/2000 | Laben et al. | |
| 6,373,055 B1 | 4/2002 | Kerr | |
| 7,112,762 B2 * | 9/2006 | Finley et al. | 219/201 |
| 7,353,994 B2 * | 4/2008 | Farrall et al. | 235/454 |
| 7,358,502 B1 * | 4/2008 | Appleby et al. | 250/370.14 |
| 7,629,400 B2 * | 12/2009 | Hyman | 524/106 |
| 7,635,828 B2 * | 12/2009 | Finley et al. | 219/494 |
| 7,843,488 B2 * | 11/2010 | Stapleton | 348/62 |
| 7,851,666 B2 * | 12/2010 | Belau et al. | 604/358 |
| 7,877,003 B2 * | 1/2011 | Dunn et al. | 396/4 |
| 2006/0049354 A1 | 3/2006 | Treado et al. | |

OTHER PUBLICATIONS

Written Opinion of the International Searching Authority for International Application No. PCT/US2010/021182, filed Jan. 15, 2010, Written Opinion dated Apr. 21, 2010 and mailed Apr. 28, 2010 (4 pgs.).
International Search Report for International Application No. PCT/US2010/021182, filed Jan. 15, 2010, International Search Report dated Apr. 21, 2010 and mailed Apr. 28, 2010 (3 pgs).
Becker, "Multicolor LWIR Focal Plane Array Technology for Space and Ground Based applications", SPIE, vol. 5564 (SPIE, Bellingham, WA) Nov. 8, 2004 (14 pgs.).

* cited by examiner

*Primary Examiner* — Yosef Kassa
(74) *Attorney, Agent, or Firm* — Christie, Parker & Hale, LLP

(57) ABSTRACT

Radiation is received from a scene impinging on at least one focal plane. A first spectral band is sampled to obtain a first band mean signal level, and either a first band image frame is collected when the first band mean signal level is at or below a first threshold, or a first image frame is collected in a first sub-band when the first band mean signal level is above the first threshold. A second sub-band is sampled to obtain a second sub-band mean signal level and a second image frame is collected in the second sub-band when the second sub-band mean signal level is at or below a second threshold. An image to be displayed is generated by combining at least two collected frames.

33 Claims, 5 Drawing Sheets

OPTIMIZED IMAGING SYSTEM FOR COLLECTION OF HIGH RESOLUTION IMAGERY

BACKGROUND

1. Field of the Invention

The present invention relates to an optimized imaging system for collection of high resolution imagery.

2. Description of Related Art

Imaging systems have been widely used to image objects at long distances using telescopes sensitive to various portions of the radiation spectrum.

A fundamental issue regarding such imaging systems is obtaining high resolution imagery. Resolution may be expensive to obtain or dangerous to collect, requiring large telescopes and/or close proximity to a potential threat. The spatial resolution inherent to an image collected by a given size telescope (e.g., based on aperture size) is determined by several factors including the wavelength of collected radiation, the dimensions of other apertures in the collection system including pixel aperture, geometric aberrations of the optical system, the spatial sampling of the image, and the stability of the collector's line of sight during image collections. Motion of the elements within the scene can cause smear, reducing the resolution of those elements unless the motion is captured in a fashion that improves how the object is sampled.

Various prior art systems have been designed to obtain imagery under various illumination conditions, including the daytime and nighttime. Obtaining high resolution imagery generally requires collecting well-sampled imagery at the shortest wavelengths of radiation possible. Prior art systems, for example, collect imagery in the daytime at spatial resolutions of inches to meters. These prior art systems utilize visible (VIS), near infrared (NIR) and medium-wave infrared (MWIR) (both reflective and thermal) regions of the spectrum to obtain daytime imagery. Prior art systems collect imagery at much lower spatial resolutions at nighttime than in daytime, by approximately a factor of 4-7 compared to daytime systems. Such prior art systems generally obtain imagery at night using MWIR (3.0 µm to 5.0 µm) and long-wave infrared (LWIR) (8.0 µm to 12.0 µm) sensors that primarily measure the thermal emissions of ambient scenes. Other prior art systems collect nighttime imagery from reflective VIS (0.3 µm to 0.7 µm), NIR (0.7 µm to 1.0 µm) and lower short-wave infrared (LSWIR) (1.0 to 2.0 µm) bands of the spectrum. A few prior art systems have obtained images of extremely hot or combusting objects at nighttime utilizing the panchromatic (PAN) (1.0 µm to 1.7 µm) and/or the LSWIR bands of the spectrum. However, images collected in the PAN waveband use intensifiers and/or designs with large pixels and are generally low in resolution. Resolution is a measure of being able to separate two or more objects in an image or to recognize an edge. Those skilled in the art recognize there is an inherent limitation to resolution for a given size telescope due to diffraction effects, though many imaging systems purposely degrade their resolution to enable wider area coverage or greater signal collection. A high resolution image, for example, is one where diffraction effects are the collecting dominant limitation to resolution.

Common knowledge instructs those skilled in the art to create sensors and systems sensitive to wavebands wherein one may find the greatest amount of useful energy to collect imagery at useful signal to noise ratios given the noise inherent to focal plane arrays and readout electronics. Accordingly, most prior art systems have focused on the VIS, NIR, MWIR, LWIR and LSWIR band to obtain imagery. These systems have generally taken advantage of the fact that more photons are available to impinge on sensors sensitive to these wavebands over other wavebands in the spectrum. Recently, prior art systems have been able to take advantage of airglow (e.g., chemiluminesence of the atmosphere) or moonglow (e.g., reflection of moonlight) to obtain degraded resolution images of distant objects.

In addition, common knowledge instructs those skilled in the art to create sensors and systems sensitive to the shortest wavelength possible while still being able to find sufficient useful energy to collect imagery. Finally, common knowledge instructs those skilled in the art to create sensors and systems where the atmosphere is transmissive at certain wavebands in the spectrum.

In part, due to such common knowledge, the upper short-wave infrared (USWIR, 2.0-2.6 um) waveband has not been widely used at night for imaging distant objects. Astronomy programs have used USWIR for study of distant stars and earth resource sensors have imaged the Earth in this band during the daytime. However, these long-range telescopes are generally required to be fixed on the distant object for great lengths of time to collect enough energy to obtain an image. In addition, the USWIR waveband has generally not been considered suitable for high resolution imaging at night as only very warm objects may be viewed at night unless a system has very degraded spatial resolution relative to the diffraction limit or collects energy for extensive (non-practical) periods of time. Consequently, it has been used for viewing combusting objects such as rocket plumes or for directly viewing man-made light sources. Moreover, technology limitations have steered research and development efforts away from systems utilizing the USWIR waveband.

Generally, the spectrum is categorized in terms of wavelengths, as may be seen from the values for each of the various wavebands. The LSWIR waveband, for instance, consists of wavelengths shorter than those of the USWIR waveband. In addition, as each of their names suggests, the LWIR, the MWIR, the USWIR and the LSWIR consist of wavelengths in the infrared part of the spectrum. The wavelengths decrease in length as one moves from the LWIR successively to the LSWIR part of the infrared spectrum.

A few prior art systems have combined data from two or more focal plane arrays to generate composite images. These prior art systems do not adapt collected image quality to ambient nighttime and/or daytime conditions. Moreover, these prior art systems do not combine nighttime images collected in the MWIR band with images collected at shorter wavelengths, provide high-resolution images of ambient temperature objects in the USWIR, collect high resolution images at night in the VIS, NIR, or LSWIR or collect high resolution images of both thermally emitted signals and reflected signals at night.

SUMMARY OF THE INVENTION

Exemplary embodiments according to the present invention provide an optimized imaging system for collection of high-resolution imagery at night. The method and system herein provides high spatial resolution imagery by collecting well-sampled imagery at the shortest wavelengths of light available in multiple wavebands while adapting the collected image quality to both man-made and natural light in various atmospheric and environmental conditions.

According to an exemplary embodiment of the present invention, there is provided a method of providing an image of a scene utilizing imaging optics, wherein the method receives radiation from the scene impinging on at least one focal plane, samples a first spectral band to obtain a first band mean signal level, the first spectral band comprising a first plurality of sub-bands, collects at least one first band image frame in the first spectral band when the first band mean signal level is at or below a first threshold, collects at least one first image frame in a first sub-band of the first plurality of sub-bands when the first band mean signal level is above the first threshold, samples a second sub-band of the first plurality of sub-bands to obtain a second sub-band mean signal level, collects at least one second sub-band image frame in the second sub-band when the second sub-band mean signal level is at or below a second threshold, and generates an image to be displayed by combining at least two collected frames.

When the second sub-band mean signal level is above the second threshold, the method may further adjust a focal length of the imaging optics until a threshold signal level is reached and collect the second image frame in the second sub-band, wherein the image to be displayed is generated by combining at least two collected frames.

The focal length of the imaging optics may also be adjusted until a threshold edge contrast ratio has been reached.

When the second sub-band mean signal level is above a third threshold, the method may further collect at least one image frame in a first portion of the second sub-band, and collect at least one image frame in a second portion of the second sub-band, wherein the image to be displayed is generated by combining at least three collected frames.

The method may further sample a second spectral band to obtain a second band mean signal level, the second spectral band comprising a second plurality of sub-bands, and collect at least one second band image frame in the second spectral band when the second band mean signal level is at or below a fourth threshold or above a fifth threshold, wherein the fifth threshold is higher than the fourth threshold, wherein the image to be displayed is generated by combining at least two collected frames.

When the second open band mean signal level is at least above the fourth threshold, the method may further collect at least one red sub-band image frame in a red sub-band of the second plurality of sub-bands for the first time portion, collect at least one green sub-band image frame in a green sub-band of the second plurality of sub-bands for the second time portion, and collect at least one blue sub-band image frame in a blue sub-band of the second plurality of sub-bands for the third time portion, wherein the image to be displayed is generated by combining at least four collected frames.

When the second open band mean signal level is at least above the fourth threshold, the method may further divide a remaining time of a maximum integration time into a first time portion, a second time portion, and a third time portion, wherein the seventh image frame is collected for the first time portion, the eighth image frame is collected for the second time portion, and the ninth image frame is collected for the third time portion.

According to another exemplary embodiment in accordance with the present invention, there is provided an imaging system for providing images of a scene, wherein the imaging system includes at least one focal plane for receiving radiation from the scene, a spectral selector configured to transmit portions of a first spectral band to the at least one focal plane, wherein the first spectral band comprises a first plurality of sub-bands, an adaptive controller configured to sample the first spectral band to obtain a first open band mean signal level, collect at least one first band image frame in the first spectral band when the first band mean signal level is at or below the first threshold, collect at least one first sub-band image frame in a first sub-band of the plurality of sub-bands when the first band mean signal level is above the first threshold, sample a second sub-band of the first plurality of sub-bands to obtain a second sub-band mean signal level, and collect at least one second sub-band image frame in the second sub-band when the second sub-band mean signal level is at or below a second threshold, and a data combiner configured to combine at least two collected frames to generate an image to be displayed.

The adaptive controller may be further configured to adjust a focal length of the image optics until a threshold signal level is reached, and collect the at least one second sub-band image frame in the second sub-band, when the second sub-band mean signal level is above the second threshold, wherein the data combiner is further configured to combine at least two collected frames to generate the image to be displayed.

The adaptive controller may be further configured to collect at least one image frame in a first portion of the second sub-band and collect at least one image frame in a second portion of the second sub-band, when the second sub-band mean signal level is above a third threshold, wherein the data combiner is further configured to combine at least three collected frames to generate the image to be displayed.

The adaptive controller may be further configured to sample a second spectral band to obtain a second band mean signal level, the second spectral band comprising a second plurality of sub-bands, and collect at least one second band image frame in the second spectral band when the second band mean signal level is at or below a fourth threshold or above a fifth threshold, wherein the fifth threshold is higher than the fourth threshold, and wherein the data combiner is further configured to combine at least two collected frames to generate the image to be displayed.

The adaptive controller may be further configured to collect at least one red sub-band image frame in a red sub-band of the second plurality of sub-bands for the first time portion, collect at least one green sub-band image frame in a green sub-band of the second plurality of sub-bands for the second time portion, and collect at least one blue sub-band image frame in a blue sub-band of the second plurality of sub-bands for the third time portion, when the second band mean signal level is at least above the fourth threshold, wherein the image to be displayed is generated by combining at least four collected frames.

The adaptive controller may be further configured to divide a remaining time of a maximum integration time into a first time portion, a second time portion, and a third time portion, and wherein the at least one red sub-band image frame is collected for the first time portion, the at least one green sub-band image frame is collected for the second time portion, and the at least one blue sub-band image frame is collected for the third time portion.

According to yet another exemplary embodiment in accordance with the present invention, there is provided a computer readable media embodying program instructions for execution by a data processing apparatus, the program instructions adapting the data processing apparatus for monitoring a network, wherein the program instructions are as follows: receive radiation from a scene impinging on at least one focal plane, sample a first spectral band to obtain a first band mean signal level, the first spectral band comprising a first plurality of sub-bands, collect at least one first band image frame in the first spectral band when the first band mean signal level is at or below a first threshold, collect at least one first sub-band image frame in a first sub-band of the first plurality of sub-bands when the first band mean signal level is above the first threshold, sample a second sub-band of the first plurality of sub-bands to obtain a second sub-band mean signal level, collect at least one second sub-band image frame in the second sub-band when the second sub-band mean signal level is at or below a second threshold, when the second sub-band mean signal level is above the second threshold, adjust a focal length of the imaging optics until a threshold signal level has been reached and collect the at least one second sub-band image frame in the second sub-band, when the second sub-band mean signal level is above a third threshold, collect at least one image frame in a first portion of the second sub-band, and collect at least one image frame in a second portion of the second sub-band, sample a second spectral band to obtain a second band mean signal level, the second spectral band comprising a second plurality of sub-bands, collect at least one second band image frame in the second spectral band when the second band mean signal level is at or below a fourth threshold or above a fifth threshold, wherein the fifth threshold is higher than the fourth threshold, when the second band mean signal level is at least above the fourth threshold, divide a remaining time of a maximum integration time into a first time portion, a second time portion, and a third time portion, collect at least one red sub-band image frame in a red sub-band of the second plurality of sub-bands for the first time portion, collect at least one green sub-band image frame in a green sub-band of the second plurality of sub-bands for the second time portion, and collect at least one blue sub-band image frame in a blue sub-band of the second plurality of sub-bands for the third time portion, and generate an image to be displayed by combining at least two collected frames.

According to yet another exemplary embodiment in accordance with the present invention, there is provided a method of obtaining imagery of ambient temperature objects at nighttime, wherein the method receives radiation from a scene impinging on at least one focal plane, samples an upper short wave infrared band of a first band to obtain an upper short wave infrared mean signal level, determines an upper short wave infrared band minimum integration time to obtain an upper short wave infrared frame from the upper short wave infrared mean signal level, collects the upper short wave infrared frame for the upper short wave infrared band minimum integration time, and generates an image to be displayed from the upper short wave infrared frame.

BRIEF DESCRIPTION OF THE DRAWINGS

A more complete appreciation of the present invention, and many of the attendant features and aspects thereof, will become more readily apparent as the invention becomes better understood by reference to the following detailed description when considered in conjunction with the accompanying drawings in which like reference symbols indicate like components, wherein.

DETAILED DESCRIPTION

The present invention will now be described more fully with reference to the accompanying drawings, in which exemplary embodiments thereof are shown. The invention may, however, be embodied in many different forms and should not be construed as being limited to the embodiments set forth herein. Rather, these embodiments are provided so that this disclosure is thorough and complete, and will fully convey the concept of the present invention to those skilled in the art.

Accordingly, there is presented an optimized imaging system for collection of high resolution imagery in accordance with exemplary embodiments of the present invention. In an exemplary embodiment, the method and system herein provide high spatial resolution imagery by collecting well-sampled imagery at the shortest wavelengths of light available in multiple wavebands while adapting to both man-made and natural light in various atmospheric and environmental conditions.

Figure 1:
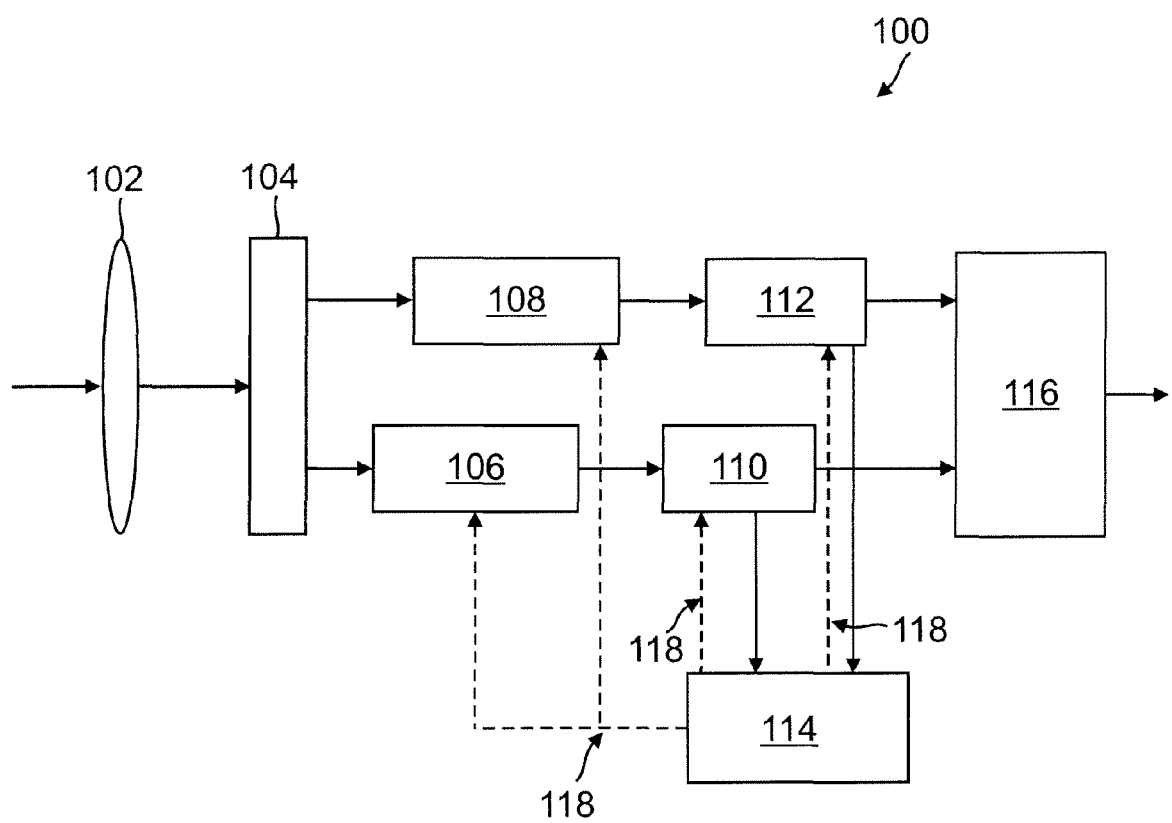
FIG. 1 is a block diagram illustrating an optimized imaging system for collection of high resolution imagery in accordance with an embodiment of the present invention.

FIG. 1 is a block diagram illustrating an optimized imaging system for collection of high resolution imagery in accordance with an embodiment of the present invention.

Referring now to FIG. 1, an optimized imaging system 100 for high resolution imagery includes an opto-mechanical imaging system 102, a spectral selector 104, a first focal plane 106, a second focal plane 108, a first readout buffer 110, a second readout buffer 112, an adaptive controller 114 and a data combiner 116.

The opto-mechanical imaging system 102 is configured to receive and relay upwelling radiation from a distant scene to the spectral selector 104. One of ordinary skill in the art would understand that the opto-mechanical imaging system 102 may be implemented in various ways, using materials and components based on the system's requirements. In an embodiment, the materials and components of the opto-mechanical imaging system 102 may be suitable to receive and relay upwelling radiation in the UV, VIS, NIR, PAN, LSWIR and/or USWIR wavebands of the spectrum (e.g., approximately 0.3 µm to 2.6 µm), or any other bands suitable to receive useful imagery. In other embodiments, the opto-mechanical imaging system 102 may be suitable to receive and relay upwelling radiation wavebands below 0.3 µm and above 2.6 µm (e.g., MWIR and LWIR).

The spectral selector 104, for example, comprises a dichroic beam splitter, configured to send all light with wavelengths above a specific threshold to the first focal plane 106 (e.g., above 1.0 µm). The spectral selector 104 may further comprise a second level spectral selector for the first focal plane 106 including an open position, a LSWIR filter and a USWIR filter, and a second spectral selector for the second focal plane 108 including an open position, a UV filter, a PAN filter, and red, blue and green filters. For example, the LSWIR filter is centered near 1.6 µm, the USWIR filter is centered near 2.3 µm, the UV filter is centered near 0.35 µm and the PAN filter covering approximately 0.5 to 0.9 µm. Accordingly, the spectral selector 104 divides the open band upwelling radiation into bands and sub-bands.

The first focal plane 106, for example, comprises an array of mercury cadmium telluride (MCT) detectors arranged as a focal plane array. In other embodiments, the first focal plane 106 comprises an array of indium antimonide (InSb) arranged as a focal plane array or any other array of detectors sensitive to detect imagery in the desired bandwidth of approximately 1.0 µm to 2.6 µm. The MCT detectors have approximately a 20 micron pitch. The second focal plane 108, for example, comprises an array of charge-coupled device silicon detectors (CCDs) arranged as a focal plane array. The CCD detectors have approximately a 7 micron pitch. In this embodiment, the second focal plane array 108 is sensitive from 0.3 µm to 1.0 µm.

However, the optimized imaging system 100 is not limited to two focal planes, but may include one focal plane array or more than two focal plane arrays. One of ordinary skill in the art would recognize that the determination of the number of focal plane arrays and their sensitivity to bandwidth is a system design choice and may vary depending on the system's requirements. In other embodiments, the arrangement of focal planes may be sensitive to wavelengths shorter than 0.3 µm or longer than 2.6 µm.

The first focal plane 106 and the second focal plane 108 must provide either a diffraction-limited optical blur or a point-spread function. Each of these focal planes must sample its point spread function with a high Q, described by the following equation:

$$Q = \frac{\lambda F}{\# P_m},$$

where $\lambda$ is the center wavelength, F/# is the focal ratio of the telescope, and $P_m$ is the metric pixel pitch. A high Q, for example, is greater than or equal to 0.5. The optical imaging system 100, for example, has a Q=1 at 1.6 um, Q≈1.5 at 2.3 um, Q=1 at 400 nm and Q=2 at 800 nm. Therefore, at a 20 km range from the sensor, the ground sample distance of the optical imaging system 100 is 11 cm for the first focal plane (e.g., the MCT array) and less than 3 cm for the second focal plane 108 (e.g., the CCD array).

The first readout buffer 110 and the second readout buffer 112 are configured to receive signals representing the scene being imaged from the first focal plane 106 and the second focal plane 108, respectively, and to buffer and transmit this data to the data combiner 116. Those skilled in the art would recognize that focal planes generate analog signals which must be digitized for storage and processing and that calibration coefficients are generally applied to the images to provide correct radiometric units. The digitization and calibration functions are not shown. The first readout buffer 110 and second readout buffer 112 format and store one or more image frames from their respective focal planes. The first readout buffer 110 and the second readout buffer 112 are also coupled to the adaptive controller 114 and configured to provide feedback data thereto. The first readout buffer 110 is configured to read out image frames at a rate of thirty frames per second. The second readout buffer 112 is configured to read out frames from the second focal plane 108 in both fast and slow read modes. For frame rates less than 10 frames per second (fps), the slow mode is used and generates about 5 e-read noise per read. For frame rates at or about 60 fps, the fast mode is used and generates about 30 e-read noise per read. The readouts for both the first focal plane 106 and the second focal plane array 108 may be non-destructive or may be reset, as is determined by the adaptive controller 114.

The adaptive controller 114 is coupled to the first focal plane 106, the second focal plane 108, the first readout buffer 110 and the second readout buffer 112. The adaptive controller 114 senses the ambient signal levels on selected frames in the open filter positions and then sets the frame rate and integration time of each focal plane as well as the spectral band of each selector to optimize spatial resolution at a minimum signal to noise ratio. The adaptive controller 114 can be preset (or alternatively, set by the system user) to optimize spatial resolution, signal to noise ratio, frame rate, and/or other image quality factors. The optimized imaging system 100 senses the upwelling radiance on a scene or any subset of pixels in a selected spectral band while using a short integration with non-destructive readouts. In other words, if there is sufficient signal to warrant additional collection after sampling the upwelling radiation, then the photons collected during the sampling interval contribute towards the final signal to noise level.

Figure 2:
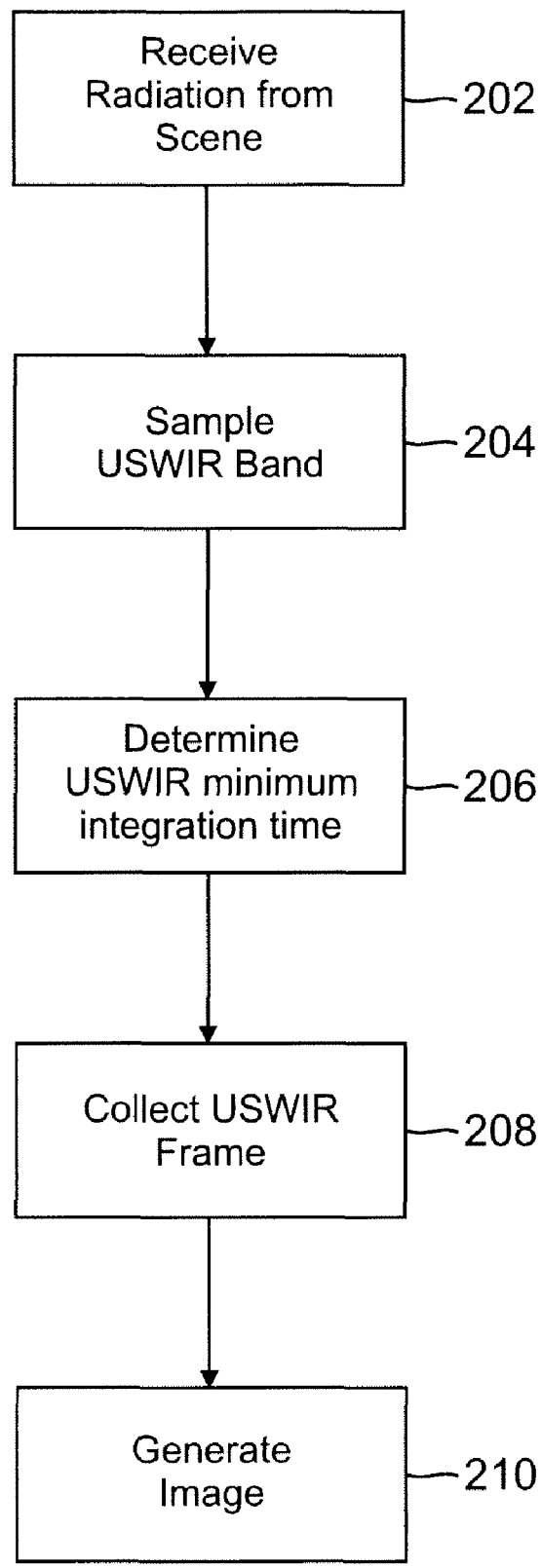
FIG. 2 is a flow diagram illustrating a method of obtaining imagery of ambient temperature objects at nighttime in accordance with an embodiment of the present invention.
Figure 3:
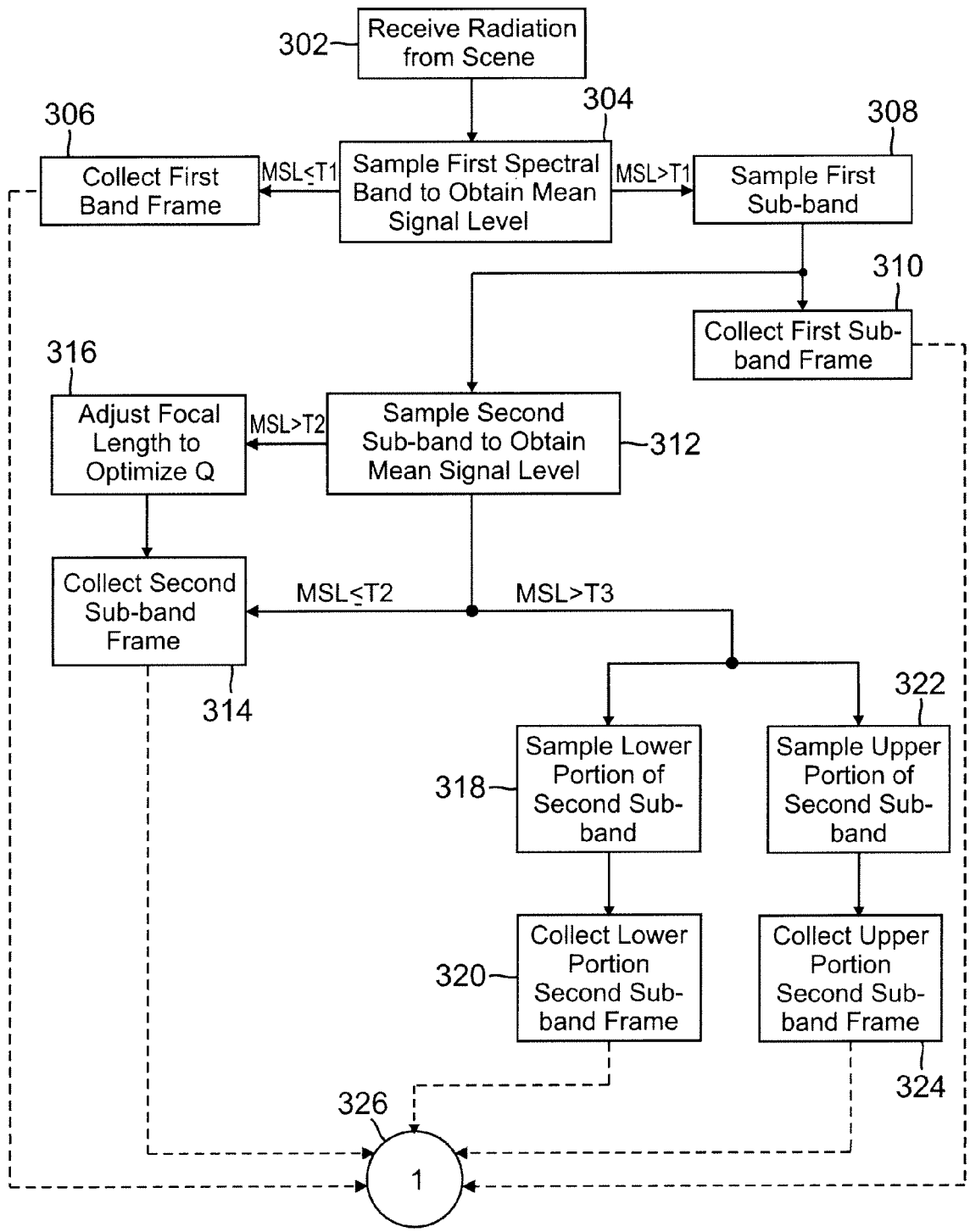
FIG. 3 is a flow diagram illustrating a method of providing an image of a scene utilizing imaging optics in accordance with an embodiment of the present invention.
Figure 4:
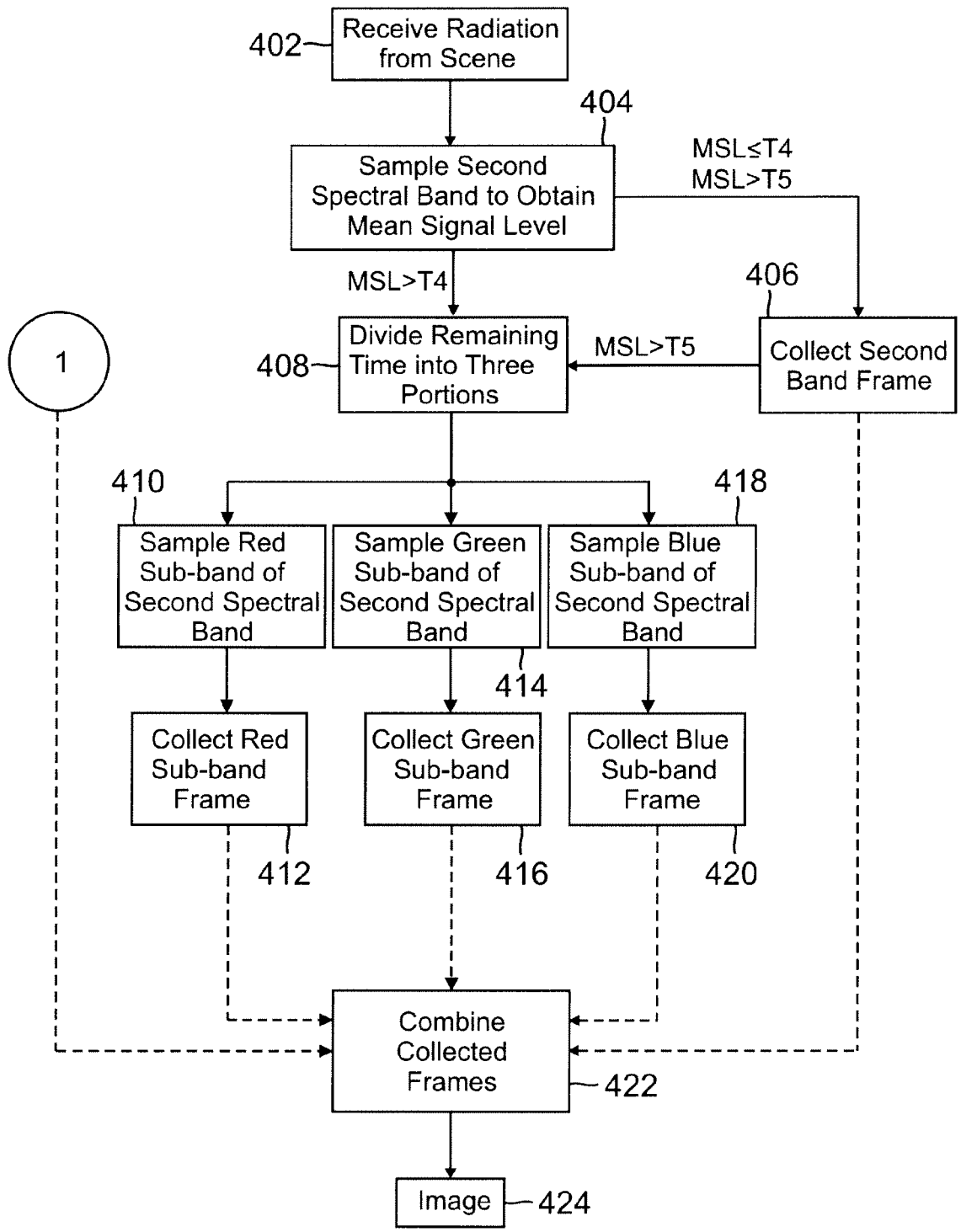
FIG. 4 is a flow diagram illustrating a method of providing an image of a scene utilizing imaging optics in accordance with an embodiment of the present invention.

Referring still to the adaptive controller 114 in FIG. 1, the adaptive controller 114, including the other elements of FIG. 1, in addition to any other necessary or desirable components not depicted in FIG. 1, is configured to perform the functionality represented in the embodiments of FIGS. 2-4. The dotted lines depicted in FIG. 1 represent control signals 118 for controlling the various components in the system. In other embodiments, the adaptive controller 114 performs only some of the functionality represented in FIGS. 2-4. The adaptive controller 114, for example, may comprise a computer readable media embodying program instructions for execution by a data processing apparatus. Such program instructions may adapt the data processing apparatus for monitoring a network. FIGS. 2-4, in part or in whole, identifies exemplary program instructions.

The data combiner 116 is coupled to the first readout buffer 110 and the second readout buffer 112 and receives image frames in the form of buffered data therefrom. The data combiner 116 registers the collected image frames, removes airglow path radiance from LSWIR images, and provides a sharpened composite image and a band ratio image. The sharpened composite image aids in the visual identification of objects. The band ratio image highlights distinctive features in the scene. The system is not necessarily limited to sharpened composite images or band ratio images, and may provide any type of image suitable for display.

U.S. Pat. No. 6,011,875 to Laben et al., entitled Process for Enhancing the Spatial Resolution of Multispectral Imagery Using PAN-Sharpening, hereby incorporated by reference in its entirety, identifies some of the various combined images that may be implemented in the data combiner 116. U.S. Pat. No. 6,373,055 to Kerr, entitled Enhanced Vision System Sensitive to Infrared Radiation, hereby incorporated by reference in its entirety, also identifies various combined images that may be implemented in the data combiner 116.

FIG. 2 is a flow diagram illustrating a method of obtaining imagery of ambient temperature objects at nighttime in accordance with an embodiment of the present invention.

Referring now to FIG. 2, at Block 202, radiation is received from the scene impinging on at least one focal plane. For example, radiation is received on a single focal plane. In another example, radiation is received on two focal planes. In an embodiment, a first focal plane corresponds to a first spectral band such that when the first focal plane receives unfiltered radiation, it receives radiation within the first spectral band (e.g., a first band signal). Likewise, a second focal plane corresponds to a second spectral band such that when the second focal plane receives unfiltered radiation, it receives radiation within the second spectral band (e.g., a second band signal). In other embodiments, the two focal planes may be sensitive to parts of the first spectral band and the second spectral band, or a single focal plane may be sensitive to a larger spectral band encompassing the first spectral band and the second spectral band.

At Block 204, an upper short wave infrared band is sampled to obtain to obtain an upper short wave infrared mean signal level (e.g., the sampled radiation collected in a filtered band of a focal plane corresponding to at least a portion of the upper short wave infrared band). The upper short wave infrared mean signal level indicates the average signal level over the upper short wave infrared band. In an aspect, the upper short wave infrared mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the upper short wave infrared mean signal level) over the scene with reasonable confidence. In addition to the upper short wave infrared mean signal level (e.g., an upper short wave infrared sample), the system may test certain regions of the scene for extremely bright regions that might saturate if the system performs a long integration time. The upper shortwave infrared sub-band generally corresponds to 2.0 μm to 2.6 μm.

Referring still to Block 204 of FIG. 2, the focal plane, for example, comprises an array of mercury cadmium telluride (MCT) detectors arranged as a focal plane array. In other embodiments, the focal plane comprises an array of indium antimonide (InSb) arranged as a focal plane array or any other array of detectors sensitive to detect imagery in the desired bandwidth of approximately 1.0 μm to 2.6 μm. The MCT detectors have approximately a 20 micron pitch, and are cooled to about 130 K to minimize or reduce dark current. The first spectral band includes a first plurality of sub-bands. Accordingly, if the first spectral band has a bandwidth of approximately 1.0 μm to 2.6 μm, a sub-band of the first plurality of sub-bands includes a portion of the first plurality of sub-bands.

At Block 206, an upper short wave infrared band minimum integration time is determined to obtain an upper short wave infrared frame from the upper short wave infrared mean signal level.

At Block 208, the upper short wave infrared frame is collected in the upper short wave infrared band.

At Block 210, an image to be displayed is generated from the upper short wave infrared frame. Alternatively, or in addition to the image to be displayed, the method may be configured to generate multiple images to be displayed in sequence. In addition, the method illustrated in FIG. 2 may be modified to incorporate wavebands other than the upper short wave infrared band. Since the method illustrated in FIG. 2 is suitable for obtaining imagery at nighttime, any imagery collected in wavebands complementary to imagery collected in the upper short wave infrared band may be especially useful to combine with the frames collected in the method illustrated in FIG. 2, but is not necessarily limited to such imagery. For example, frames collected at nighttime in the LSWIR band may be complementary with frames collected at nighttime in the USWIR. This is because it is complementary to fuse or combine reflective-based signals with thermal-based signals (LSWIR signals collected at nighttime are generally dominated by the reflective component of the signal, whereas USWIR signals collected at nighttime are generally dominated by the thermal component of the signal).

FIG. 3 is a flow diagram illustrating a method of providing an image of a scene utilizing imaging optics in accordance with an embodiment of the present invention.

Referring now to FIG. 3, at Block 302, radiation is received from the scene impinging on at least one focal plane. For example, radiation is received on two focal planes. In an embodiment, a first focal plane corresponds to a first spectral band such that when the first focal plane receives unfiltered radiation, it receives radiation within the first spectral band (e.g., a first band signal). Likewise, a second focal plane corresponds to a second spectral band such that when the second focal plane receives unfiltered radiation, it receives radiation within the second spectral band (e.g., a second band signal).

At Block 304, the first spectral band is sampled to obtain a first band mean signal level (e.g., the sampled radiation collected in an open band of the first focal plane). The system generally utilizes a short integration interval to obtain the first band mean signal to gauge how long the system must integrate the scene to achieve a minimum signal to noise ratio. In an aspect, the first band mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the first band mean signal level) over the scene with reasonable confidence. In addition to an open band sample, the system may test certain regions of the scene for extremely bright regions that might saturate if the system performs a long integration time.

Referring still to Block 304 of FIG. 2, the first focal plane, for example, comprises an array of mercury cadmium telluride (MCT) detectors arranged as a focal plane array. In other embodiments, the first focal plane 306 comprises an array of indium antimonide (InSb) arranged as a focal plane array or any other array of detectors sensitive to detect imagery in the desired bandwidth of approximately 1.0 μm to 2.6 μm. The MCT detectors have approximately a 20 micron pitch, and are cooled to about 130 K to minimize or reduce dark current. The first spectral band includes a first plurality of sub-bands. Accordingly, if the first spectral band has a bandwidth of approximately 1.0 μm to 2.6 μm, a sub-band of the first plurality of sub-bands includes a portion of the first plurality of sub-bands.

At Block 306, a first band image frame is collected when the first band mean signal level is at or below a first threshold. The first threshold, for example, is a predetermined threshold that is set by a system user. The first threshold may also be adjustable depending on the system requirements and overall desired image quality. The first band image frame is collected by integrating over the first spectral band for a time period determined by the first band mean signal level. In other words, the system must integrate signal contained in the first spectral band for a time period sufficient to obtain a useable frame. The significance of the first band mean signal level being at or below the first threshold is that there is insufficient signal level in the first spectral band to obtain useable frames in a sub-band of the first plurality of sub-bands. Accordingly, integrating over the entire bandwidth of the first spectral band generates the best useable frame given the available radiation from the scene, since the average available radiation from the scene does not exceed the first threshold.

At Block 308, a first sub-band of the first plurality of sub-bands is sampled to obtain a first sub-band mean signal level when the first band mean signal level is above the first threshold. The first sub-band mean signal level indicates the average signal level over the first sub-band of the first plurality of sub-bands. In an aspect, the first sub-band mean signal level is read but not destroyed so that it contributes to the overall signal level. This may prove to be important because the system may free up additional integration time to integrate signal contained in other spectral bands or sub-bands thereof.

A nominal sample time is 0.1 seconds, although the sample time may be set to other intervals. One of ordinary skill in the art would understand that the sample time is chosen to find the average signal level (e.g., the first sub-band mean signal level) over the scene with reasonable confidence. In addition to the first sub-band sample, the system may test certain regions of the scene for extremely bright regions that might saturate if the system performs a long integration time. The first sub-band of the first plurality of sub-bands, for example, is an upper short-wave infrared sub-band or a portion thereof. The upper short-wave infrared sub-band generally corresponds to 2.0 μm to 2.6 μm. Although the first sub-band of the first plurality of sub-bands is identified as the upper short wave infrared sub-band in FIG. 3, in other embodiments, the first sub-band may include all or part of other bands or sub-bands in any part of the spectrum where there exists available radiation to generate a useful image frame.

At Block 310, a first sub-band image frame (e.g., a first frame) is collected in the first sub-band of the first plurality of sub-bands. As seen in FIG. 2, the first sub-band image frame is collected only when the first band mean signal level is above the first threshold. The significance of the first band mean signal level being greater than the first threshold is that there is sufficient signal level to obtain a useable frame (e.g., the first sub-band image frame). Accordingly, one of ordinary skill in the art would recognize that the first threshold is chosen to ensure that a useable frame is collected.

At Block 312, a second sub-band of the first plurality of sub-bands is sampled to obtain a second sub-band mean signal level. The second sub-band mean signal level indicates the average radiation available within the second sub-band. In an aspect, the second sub-band mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the second sub-band mean signal level) over the scene with reasonable confidence. In addition to the second sub-band sample, the system may test certain regions of the scene for extremely bright regions that might saturate if the system performs a long integration time. The second sub-band of the first plurality of sub-bands, for example, is a lower short-wave infrared sub-band or a portion thereof. The lower short-wave infrared sub-band generally corresponds to 1.0 μm to 2.0 μm. Although the second sub-band of the first plurality of sub-bands is identified as the lower short wave infrared sub-band in FIG. 3, in other embodiments, the second sub-band may include all or part of other bands or sub-bands in any part of the spectrum where there exists available radiation to generate a useful image frame.

At Block 314, a second sub-band image frame (e.g., a second frame) is collected in the second sub-band of the first plurality of sub-bands when the second sub-band mean signal level is at or below a second threshold. The second threshold, for example, is a predetermined threshold that is set by a system user. The second threshold may also be adjustable depending on the system requirements and overall desired image quality. The second sub-band image frame is collected by integrating over the second sub-band for a time period determined by the second sub-band mean signal level. In other words, the system must integrate signal contained in the second sub-band for a time period sufficient to obtain a useable frame. The significance of the second sub-band mean signal level being at or below the second threshold is that there is insufficient signal level in the second sub-band to obtain useable frames in the second sub-band. Accordingly, integrating over the entire second sub-band generates a useable frame given the available radiation from the scene, since the average available radiation from the scene does not exceed the second threshold.

At Block 316, a focal length of the imaging optics is adjusted to balance image edge contrast with amount of collected signal. The result of this balance is to optimize Q in each sub-band. For example, the focal length may be adjusted to obtain a maximum amount of signal level. Alternatively, the focal length may be adjusted to obtain a highest image edge contrast. In another aspect, the focal length may be adjusted such that a threshold image edge contrast is reached while a threshold signal level is reached. Once the focal length is adjusted, the second image frame is collected in the second sub-band of the first plurality of sub-bands, as in Block 314. The second image frame is collected by integrating over the second sub-band for a time period determined by the second sub-band mean signal level. In other words, the system must integrate signal contained in the second sub-band for a time period sufficient to obtain a useable frame. Here, the significance of the second sub-band mean signal level being above the second threshold is that there is sufficient signal level in the second sub-band to obtain useable frames in the second sub-band after adjusting the focal length to optimize Q in each sub-band. Accordingly, integrating over the second sub-band generates a useable frame given the available radiation from the scene, since the average available radiation from the scene exceeds the second threshold.

At Block 318, a lower half of the second sub-band is sampled to obtain a mean signal level in the lower half of the second sub-band when the second sub-band mean signal level is above a third threshold. The mean signal level of the lower half of the second sub-band indicates the average radiation available within the lower half of the second sub-band. In an aspect, the mean signal level in the lower half of the second sub-band is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the mean signal level in the lower half of the second sub-band mean signal level) over the scene with reasonable confidence. In addition to the sample of the lower half of the second sub-band, the system may test certain regions of the scene for extremely bright regions that might saturate if the system performs a long integration time. The third threshold, for example, is a predetermined threshold that is set by a system user. The third threshold may also be adjustable depending on the system requirements and overall desired image quality.

At Block 320, a lower portion second sub-band image frame is collected in the lower half of the second sub-band. The lower portion second sub-band image frame is collected by integrating over the lower half of the second sub-band for a time period determined by the mean signal level of the lower half of the second sub-band. In other words, the system must integrate signal contained in the lower half of the second sub-band for a time period sufficient to obtain a useable frame. The significance of the second sub-band mean signal level being above the third threshold is that there is sufficient signal level in the lower half of the second sub-band to obtain useable frames in the lower half of the second sub-band. Accordingly, integrating over the lower half of the second sub-band generates a useable frame given the available radiation from the scene, since the average available radiation from the scene exceeds the third threshold.

At Block 322, an upper half of the second sub-band is sampled to obtain a mean signal level in the upper half of the second sub-band when the second sub-band mean signal level is above the third threshold. The mean signal level of the upper half of the second sub-band indicates the average radiation available within the upper half of the second sub-band. In an aspect, the mean signal level in the upper half of the second sub-band is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the mean signal level in the upper half of the second sub-band mean signal level) over the scene with reasonable confidence. In addition to the sample of the upper half of the second sub-band, the system may test certain regions of the scene for extremely bright regions that might saturate if the system performs a long integration time.

At Block 324, an upper portion second sub-band image frame is collected in the upper half of the second sub-band. The upper portion second sub-band image frame is collected by integrating over the upper half of the second sub-band for a time period determined by the mean signal level of the upper half of the second sub-band. In other words, the system must integrate signal contained in the upper half of the second sub-band for a time period sufficient to obtain a useable frame. As with the lower half of the second sub-band, the significance of the second sub-band mean signal level being above the third threshold is that there is sufficient signal level in the upper half of the second sub-band to obtain useable frames in the upper half of the second sub-band. Accordingly, integrating over the upper half of the second sub-band generates a useable frame given the available radiation from the scene, since the average available radiation from the scene exceeds the third threshold.

At Block 326, (1) may be integrated with FIG. 4, such that all collected frames in either the first spectral band (or any sub-bands therein) or the second spectral band (or any sub-bands therein) are combined to generate an image to be displayed. Alternatively, the collected frames from FIG. 3 may be combined without the collected frames from FIG. 4. FIG. 3 depicts varying levels of thresholds such that the higher the average available radiation from a scene, the greater the number of sub-bands are to be combined to generate the image to be displayed. Accordingly, based on the average available radiation, the output of (1) may be one of the following: the first band frame; the first sub-band frame; the first sub-band frame and the second sub-band frame; the first sub-band frame, the lower portion second sub-band frame and the upper portion second sub-band frame; and the second sub-band frame, the lower portion second sub-band frame and the upper portion second sub-band frame. Such outputs are combined with any collected frames resulting from the output of FIG. 4, to generate an image to be displayed. Various other combinations of bands and/or sub-bands would be understood by one of ordinary skill in the art.

FIG. 4 is a flow diagram illustrating a method of providing an image of a scene utilizing imaging optics in accordance with an embodiment of the present invention.

Referring now to FIG. 4, at Block 402, radiation is received from the scene impinging on at least one focal plane. For example, radiation is received on a second focal plane (e.g., integrated with the method according to FIG. 3). In another example, radiation is received on two focal planes. In an embodiment, a first focal plane corresponds to a first spectral band such that when the first focal plane receives unfiltered radiation, it receives radiation within the first spectral band (e.g., a first band signal). Likewise, a second focal plane corresponds to a second spectral band such that when the second focal plane receives unfiltered radiation, it receives radiation within the second spectral band (e.g., a second band signal). In other embodiments, the two focal planes may be sensitive to parts of the first spectral band and the second spectral band, or a single focal plane may be sensitive to a larger spectral band encompassing the first spectral band and the second spectral band.

At Block 404, the second spectral band is sampled to obtain a second band mean signal level (e.g., the sampled radiation collected in an open band of the second focal plane 108). The system generally utilizes a short integration interval to obtain the second band mean signal to gauge how long the system must integrate the scene to achieve a minimum signal to noise ratio. In an aspect, the second band mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the second band mean signal level) over the scene with reasonable confidence. In addition to an open band sample, the system may test certain regions of the scene for extremely bright regions that may saturate if the system performs a long integration time.

Referring still to Block 404, the second focal plane 108, for example, comprises an array of charge-coupled device (CCD) silicon detectors arranged as a focal plane array. In other embodiments, the second focal plane 108 comprises any other array of detectors sensitive to detect imagery in the desired bandwidth of approximately 0.3 µm to 1.0 µm. The CCD detectors have approximately a 7 micron pitch, and are cooled to about 200 K to minimize or reduce dark current. The second spectral band includes a second plurality of sub-bands. Accordingly, if the second spectral band has a bandwidth of approximately 0.3 µm to 1.0 µm, a sub-band of the second plurality of sub-bands includes a portion of the second plurality of sub-bands. Although the second spectral band is identified as the band including 0.3 µm to 1.0 µm, in other embodiments, the second spectral band may include all or part of other bands or sub-bands in any part of the spectrum where there exists available radiation to generate a useful image frame.

At Block 406, a second band image frame is collected when the second band mean signal level is at or below a fourth threshold or above a fifth threshold. The second band image frame is collected by integrating over the entire second spectral band for a time period determined by the second band mean signal level. In other words, the system must integrate signal contained in the second spectral band for a time period sufficient to obtain a useable frame. The significance of the second band mean signal level being at or below the fourth threshold is that there is sufficient signal level in the second spectral band to obtain useable frames in the second spectral band, but not sufficient signal level in the second spectral band to obtain useful frames in sub-bands of the second plurality of sub-bands. The significance of the second band mean signal level being above the fifth threshold is that there is sufficient signal level in the second spectral band to obtain useful frames in the second spectral band and sufficient signal level in sub-bands of the second plurality of sub-bands to obtain useful frames in the second plurality of sub-bands. Accordingly, integrating over the second spectral band generates a useable frame given the available radiation from the scene, since the average available radiation from the scene is at least enough to collect a frame in the second spectral band.

At Block 408, a remaining time of a maximum integration time is divided into a first time portion, a second time portion and a third time portion when the second band mean signal level is above the fourth threshold. The maximum integration time is a system parameter that depends on the specific application and desired results. For example, the maximum integration time is set to avoid smear or other undesirable characteristics resulting from too long of time spent integrating. The remaining time is the difference between the maximum integration time and the time spent integrating during preceding sampling and/or frame collecting. In other embodiments, the remaining time is divided into two portions or four or more portions, depending on the sub-bands remaining to be sampled and collected. The significance of the second band mean signal level being above the fourth threshold is that there is sufficient signal level in sub-bands of the second spectral band to obtain useful frames in the second plurality of sub-bands, but not sufficient signal level in the second spectral band to obtain useful frames in the entire second spectral band and sub-bands of the second spectral band.

As was described in reference to Block 406, when the second band mean signal level is above the fifth threshold, the second band image frame is collected. In addition, when the second band mean signal level is above the fifth threshold, at Block 408, the remaining time of the maximum integration time is divided into the first time portion, the second time portion and the third time portion. The significance of the second band mean signal level being above the fifth threshold is that there is sufficient signal level in the second spectral band as well as sub-bands of the second spectral band to obtain useful frames in the entire second spectral band and sub-bands of the second spectral band.

At Block 410, a red sub-band of the second plurality of sub-bands is sampled to obtain a red sub-band mean signal level when the second band mean signal level is at least above the fourth threshold. The second band mean signal level indicates the average radiation available within the second spectral band. In an aspect, the red sub-band band mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the red sub-band mean signal level) over the scene with reasonable confidence. In addition to the red sub-band sample, the system may test certain regions of the scene for extremely bright regions that may saturate if the system performs a long integration time. The red sub-band, for example, corresponds to 0.6 μm to 0.7 μm.

At Block 412, a red sub-band image frame is collected in the red sub-band of the second plurality of sub-bands when the second band mean signal level is above the fifth threshold. The red sub-band image frame is collected by integrating over the red sub-band for at least a time period determined by the red sub-band mean signal level. In other words, the system must integrate signal contained in the red sub-band for a time period sufficient to obtain a useable frame. The significance of the red sub-band mean signal level being above the fifth threshold is that there is sufficient signal level in the red sub-band to obtain useable frames in the red sub-band. Accordingly, integrating over the red sub-band generates a useable frame given the available radiation from the scene, since the average available radiation from the scene exceeds the fifth threshold.

At Block 414, a green sub-band of the second plurality of sub-bands is sampled to obtain a green sub-band mean signal level when the second band mean signal level is above the fifth threshold (logically, if the second band mean signal level is above the fifth threshold, the second band mean signal level is also above the sixth threshold). The second band mean signal level indicates the average radiation available within the second spectral band. In an aspect, the green sub-band band mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the green sub-band mean signal level) over the scene with reasonable confidence. In addition to an green sub-band sample, the system may test certain regions of the scene for extremely bright regions that may saturate if the system performs a long integration time. The green sub-band, for example, corresponds to 0.5 μm to 0.6 μm.

At Block 416, a green sub-band image frame is collected in the green sub-band of the second plurality of sub-bands when the second band mean signal level is above the fifth threshold. The green sub-band image frame is collected by integrating over the green sub-band for at least a time period determined by the green sub-band mean signal level. In other words, the system must integrate signal contained in the green sub-band for a time period sufficient to obtain a useable frame. The significance of the green sub-band mean signal level being above the sixth threshold is that there is sufficient signal level in the green sub-band to obtain useable frames in the green sub-band. Accordingly, integrating over the green sub-band generates a useable frame given the available radiation from the scene, since the average available radiation from the scene exceeds the fifth threshold.

At Block 418, a blue sub-band of the second plurality of sub-bands is sampled to obtain a blue sub-band mean signal level when the second band mean signal level is above the fifth threshold (logically, if the second band mean signal level is above the fifth threshold, the second band mean signal level is also above the sixth threshold). The second band mean signal level indicates the average radiation available within the second spectral band. In an aspect, the blue sub-band band mean signal level is read but not destroyed so that it contributes to the overall signal level. This may prove to be important because the system may free up additional integration time to integrate signal contained in other spectral bands or sub-bands thereof. A nominal sample time is 0.1 seconds, although the sample time may be set to other intervals. One of ordinary skill in the art would understand that the sample time is chosen to find the average signal level (e.g., the blue sub-band mean signal level) over the scene with reasonable confidence. In addition to the blue sub-band sample, the system may test certain regions of the scene for extremely bright regions that may saturate if the system performs a long integration time. The blue sub-band, for example, corresponds to 0.4 μm to 0.5 μm.

At Block 420, a blue sub-band image frame is collected in the blue sub-band of the second plurality of sub-bands when the second band mean signal level is above the fifth threshold. The blue sub-band image frame is collected by integrating over the blue sub-band for at least a time period determined by the blue sub-band mean signal level. In other words, the system must integrate signal contained in the blue sub-band for a time period sufficient to obtain a useable frame. The significance of the blue sub-band mean signal level being above the fifth threshold is that there is sufficient signal level in the blue sub-band to obtain useable frames in the blue sub-band. Accordingly, integrating over the blue sub-band generates a useable frame given the available radiation from the scene, since the average available radiation from the scene exceeds the fifth threshold.

Referring now to Blocks 410-420, if the red sub-band image frame, the green sub-band image frame and the blue sub-band image frame are the final frames to be collected, the red sub-band image frame is collected for the first time period, the green sub-band image frame is collected for the second time period, and the blue sub-band image frame is collected for the third time period. This ensures that the final frames to be collected efficiently utilize the remaining time of the maximum integration time. In this embodiment, it may be unnecessary to sample the red sub-band, the green sub-band and the blue sub-band before collecting the red sub-band image frame, the green sub-band image frame and the blue sub-band image frame. This is because the amount of signal measured in the open band may be used by the adaptive controller to set a sequence of image collections in red, green, and blue without sampling each one individually.

However, in other embodiments, the red sub-band image frame, the green sub-band image frame and the blue sub-band image frame may not be the final frames to be collected. In those embodiments, the system and method thereof are designed to determine how many common frames exist and to divide the remaining time accordingly. If there are no common frames (e.g., the red sub-band image frame, the green sub-band image frame and the blue sub-band image frame, or the upper half and the lower half of the second sub-band of the first plurality of sub-bands), the final frame will be integrated for the remaining time.

Referring still to Blocks 410-420, the bands have been characterized as corresponding to the red band (0.6 μm to 0.7 μm), the green band (0.5 μm to 0.6 μm) and the blue band (0.4 μm to 0.5 μm). However, in other embodiments, it may be advantageous to furcate a band or final band (e.g., to use up the remaining time in the maximum integration time) into three or more sub-bands before collecting frames in each of the sub-bands. One of ordinary skill in the art would recognize that various physical or system properties may dictate which band or bands to furcate.

At Block 422, all collected frames are combined to generate an image to be displayed. As was described in reference to FIG. 3, the (1) depicted as the output of FIG. 3 may be incorporated into FIG. 4 such that all collected frames from the output of FIG. 3 are combined with all of the collected frames from the output of FIG. 4. According to an aspect disclosed in FIGS. 3 and 4, the first band image frame and the second band image frame are combined to generate the image to be displayed. According to another aspect, the first band image frame, the red sub-band image frame, the green sub-band image frame and the blue sub-band image frame are combined to generate the image to be displayed. According to another aspect, the first band image frame, the second band image frame, the red sub-band image frame, the green sub-band image frame and the blue sub-band image frame are combined to generate the image to be displayed.

Referring still to Block 422, according to another aspect, the first sub-band image frame and the second band image frame are combined to generate the image to be displayed. According to another aspect, the first sub-band image frame, the red sub-band image frame, the green sub-band image frame and the blue sub-band image frame are combined to generate the image to be displayed. According to another aspect, the first image frame, the second band image frame, the red sub-band image frame, the green sub-band image frame and the blue sub-band image frame are combined to generate the image to be displayed.

Referring still to Block 422, according to another aspect, the second sub-band image frame and the second band image frame are combined to generate the image to be displayed. According to another aspect, the second sub-band image frame, the red sub-band image frame, the green sub-band image frame and the blue sub-band image frame are combined to generate the image to be displayed. According to another aspect, the second sub-band image frame, the second band image frame, the red sub-band image frame, the green sub-band image frame and the blue sub-band image frame are combined to generate the image to be displayed.

Referring still to Block 422, according to another aspect, the lower portion second sub-band image frame, the upper portion second sub-band image frame and the second band image frame are combined to generate the image to be displayed. According to another aspect, the lower portion second sub-band image frame, the upper portion second sub-band image frame, the red sub-band image frame, the green sub-band image frame and the blue sub-band image frame are combined to generate the image to be displayed. According to another aspect, the lower portion second sub-band image frame, the upper portion second sub-band image frame, the second band image frame, the red sub-band image frame, the green sub-band image frame and the blue sub-band image frame are combined to generate the image to be displayed.

Referring still to Block 422, according to another aspect, the first sub-band image frame, the second sub-band image frame and the second band image frame are combined to generate the image to be displayed. According to another aspect, the first sub-band image frame, the second sub-band image frame, the red sub-band image frame, the green sub-band image frame and the blue sub-band image frame are combined to generate the image to be displayed. According to another aspect, the first sub-band image frame, the second sub-band image frame, the second band image frame, the red sub-band image frame, the green sub-band image frame and the blue sub-band image frame are combined to generate the image to be displayed.

Referring still to Block 422, according to another aspect, the first sub-band image frame, the lower portion second sub-band image frame, the upper portion second sub-band image frame and the second band image frame are combined to generate the image to be displayed. According to another aspect, the first sub-band image frame, the lower portion second sub-band image frame, the upper portion second sub-band image frame, the red sub-band image frame, the green sub-band image frame and the blue sub-band image frame are combined to generate the image to be displayed. According to another aspect, the first sub-band image frame, the lower portion second sub-band image frame, the upper portion second sub-band image frame, the second band image frame, the red sub-band image frame, the green sub-band image frame and the blue sub-band image frame are combined to generate the image to be displayed.

Referring still to Block 422, according to another aspect, the second sub-band image frame, the lower portion second sub-band image frame, the upper portion second sub-band image frame and the second band image frame are combined to generate the image to be displayed. According to another aspect, the second sub-band image frame, the lower portion second sub-band image frame, the upper portion second sub-band image frame, the red sub-band image frame, the green sub-band image frame and the blue sub-band image frame are combined to generate the image to be displayed. According to another aspect, the second sub-band image frame, the lower portion second sub-band image frame, the upper portion second sub-band image frame, the second band image frame, the red sub-band image frame, the green sub-band image frame and the blue sub-band image frame are combined to generate the image to be displayed.

Referring still to Block 422, such combinations of frames may result in sharpened composite images, band ratio images, or any other types of images suitable for display (shown in Block 424). The sharpened composite image aids in the visual identification of objects. The band ratio image highlights distinctive features in the scene.

At Block 424, the image is read out to be displayed. Generally, the image is configured to be a digital image and to be displayed on any number of digital displays. However, the image and/or the display system or method are not necessarily limited to digital images or digital displays.

Referring still to FIGS. 3 and 4, a number of lines appear as dashed lines to signify that a frame may be collected and combined with other frames depending on the sampled radiation and the threshold determinations (e.g., the first through fifth thresholds). Accordingly, some of the frames will not be combined in Block 422 depending on whether the sampled radiation meets or exceeds the thresholds, at least with respect to the exemplary embodiment in FIGS. 3 and 4. The thresholds generally increase in relative signal level from the first threshold to the fifth threshold, but the thresholds are not necessarily limited thereto. While the various combinations have been thoroughly discussed in reference to FIGS. 3 and 4, other combinations may exist should a system designer decide to modify the relative levels of such thresholds or to make modifications to the logic determinations in FIGS. 3 and 4. The method and system herein is intended to cover all such variations.

Figure 5:
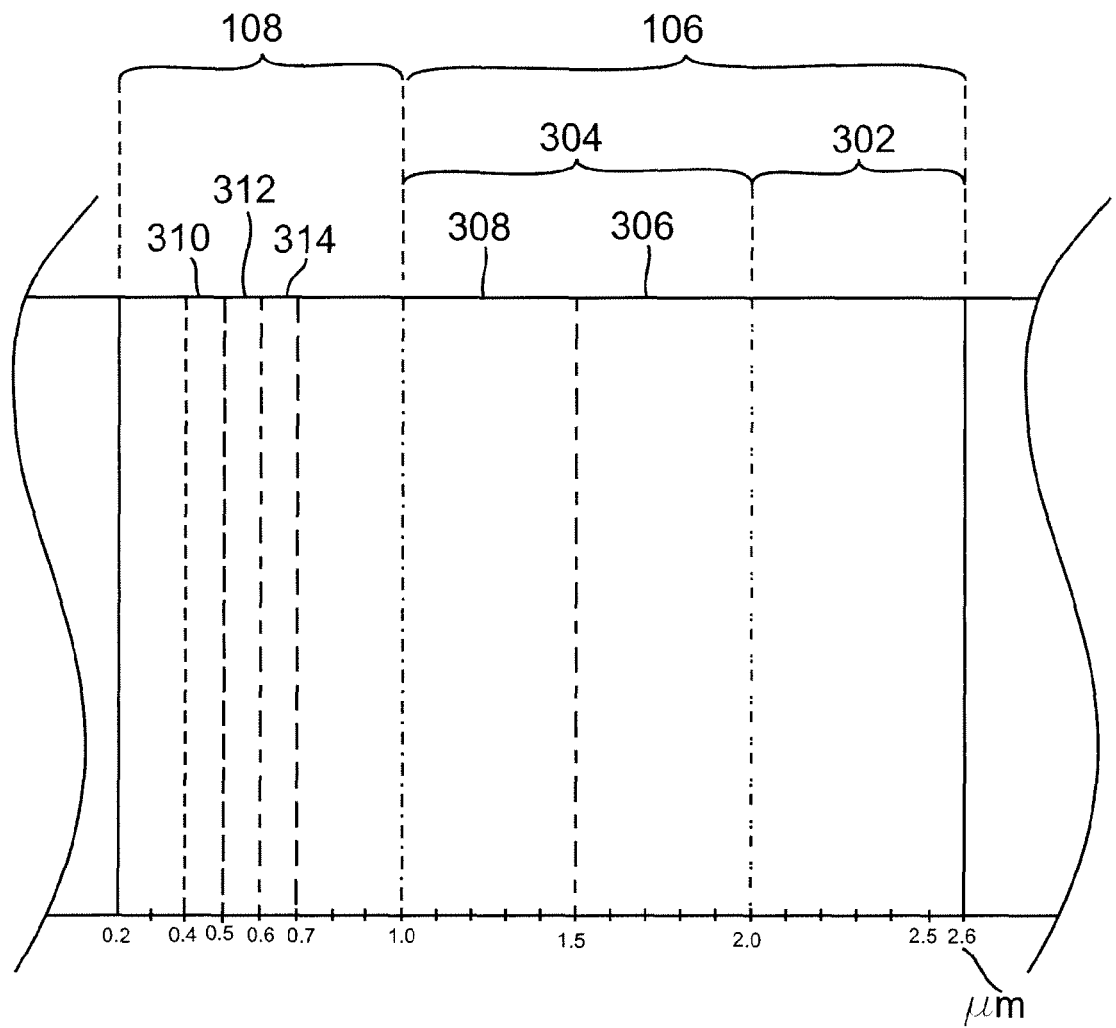
FIG. 5 is a graph illustrating exemplary wavebands that are sampled according to the embodiments of the present invention in FIGS. 2-4.

FIG. 5 is a graph illustrating exemplary wavebands that are sampled according to the exemplary embodiments of FIGS. 2-4. FIG. 5 identifies the first focal plane 106 covering a waveband of 1.0 µm to 2.6 µm and the second focal plane 108 covering a waveband of 0.3 µm to 1.0 µm. Within the waveband covered by the first focal plane array, an upper short-wave infrared waveband 502 (e.g., the first sub-band of the first plurality of sub-bands) and a lower short-wave infrared waveband 504 (e.g., the second sub-band of the first plurality of sub-bands) is depicted. Within the lower short-wave infrared waveband 504, an upper half of the lower short-wave infrared waveband 506 (e.g., the upper half of the second sub-band of the first plurality of sub-bands) and a lower half of the lower short-wave infrared waveband 508 (e.g., the lower half of the second sub-band of the first plurality of sub-bands) is depicted. Within the waveband covered by the second focal plane array, a blue waveband 510 (e.g., the blue sub-band of the second plurality of sub-bands), a green waveband 512 (e.g., the green sub-band of the second plurality of sub-bands) and a red waveband 514 (e.g., the red sub-band of the second plurality of sub-bands) is depicted. The spectral selector 104 of FIG. 1 filters the upwelling radiation received by the opto-mechanical imaging system 102 to pass wavebands corresponding to the sub-bands in FIG. 3 to the data combiner 116 to be combined into a composite image.

However, one of ordinary skill in the art would recognize that the system and method thereof presented herein is not limited to the specified bands and sub-bands described in reference to FIGS. 3 and 4, but may include additional bands or sub-bands or portions thereof not specifically mentioned. For example, the bands or sub-bands may include wavelengths less than 0.3 µm or greater than 2.6 µm, or may include part or all of each waveband depicted in FIG. 5.

Accordingly, referring to FIGS. 1-4, one of ordinary skill in the art would recognize that the method and system herein may be modified to include sampling and/or collecting bands and/or sub-bands thereof in wavebands not covered in FIGS. 1-4. For example, the first focal plane 106 may be sensitive to bands that cover 0.3 µm to 2.6 µm. The second focal plane 108 may be sensitive to bands that cover 2.6 µm to 5.0 µm (e.g., bands above the upper short wave infrared band, including the MWIR band (3.5 µm to 5.0 µm). Although not explicitly depicted in FIGS. 2-5, any of the methods depicted in FIGS. 2-4 may be modified to collect frames in the MWIR band.

Generally speaking, collecting frames in the MWIR band would not require sampling the MWIR band to obtain a minimum integration time since in most, if not all situations, there is sufficient radiation present from a scene to collect useful frames in the MWIR band. In addition, it may be advantageous for some system designs to collect frames in the PAN band (e.g., 0.45 to 0.9). Depending on atmospheric conditions, the type of scene or target, or the time of day or night, it may be advantageous to collect frame(s) in the MWIR band while collecting frame(s) in the VIS, NIR, LSWIR and USWIR. For example, with moving targets, collecting MWIR frames may be able to frame sufficiently fast to "freeze" the motion of the target. So even though the MWIR image is intrinsically more blurry it has much higher signal levels, which support rapid framing (e.g. 60 Hz or faster). Even for static images/targets the higher signal to noise ratio (e.g., higher signal, less noise) of the MWIR image can be fused with USWIR and/or LSWIR frames which will generally have sharper resolution (crisper imagery) but with lower signal to noise ratio (e.g., lower signal, higher noise). Moreover, it is advantageous to combine thermal-based imagery (e.g., frames with a dominant thermal component) with reflective-based imagery (e.g., frames with a dominant reflective component) to complement the strengths of each type of frame. Depending on the temperature of the scene or target, the thermal or reflective component of each of the bands' frames may be dominant. For example, with normal (ambient) earth temperatures, the USWIR band is dominated by the thermal component. With combustive or very hot temperatures (e.g., burning or high-temperature electrical arcing), the USWIR and the LSWIR bands are dominated by the thermal component. With artificial or man-made light (e.g., streetlamps, etc.), the USWIR thermal component is significantly less than the reflective component. Accordingly, combining reflective or thermal-based MWIR frames with other frames having thermal-based dominance or reflective-based dominance, respectively, may result in imagery having complementary strengths from each type of frame.

Referring to FIGS. 2-4, FIGS. 2-4 identify a scenario where only one frame is collected for each of the Blocks. However, one of ordinary skill in the art would recognize that the system and method herein is not necessarily limited to collecting only one frame per band and/or sub-band, but may be adapted to collect a specified number of frames for all or only some of the bands and/or sub-bands. In addition, one of ordinary skill in the art would recognize that in other embodiments, the system and method may be designed to collect a single frame in each potential band and/or sub-band until a threshold signal level has been reached. The system and method herein in accordance with the present invention is not limited to single frames nor is it limited to a specified type or duration of time to collect each frame.

Therefore, there is presented an optimized imaging system for collection of high resolution imagery in accordance with exemplary embodiments of the present invention. In an exemplary embodiment, the method and system herein provides high spatial resolution imagery by collecting well-sampled imagery at the shortest wavelengths of light available in multiple wavebands while adapting to both man-made and natural light in various atmospheric and environmental conditions.

What is claimed is:

1. A method of providing an image of a scene utilizing imaging optics, the method comprising:
   receiving radiation from the scene impinging on at least one focal plane;
   sampling a first spectral band to obtain a first band mean signal level, the first spectral band comprising a first plurality of sub-bands;
   collecting at least one first band image frame in the first spectral band when the first band mean signal level is at or below a first threshold;
   collecting at least one first image frame in a first sub-band of the first plurality of sub-bands when the first band mean signal level is above the first threshold;
   sampling a second sub-band of the first plurality of sub-bands to obtain a second sub-band mean signal level;
   collecting at least one second sub-band image frame in the second sub-band when the second sub-band mean signal level is at or below a second threshold; and
   generating an image to be displayed by combining at least two collected frames.

2. The method of claim 1, the method further comprising:
   determining a first band minimum integration time to obtain the first band image frame from the first band mean signal level.

3. The method of claim 1, the method further comprising:
   sampling the first sub-band of the first plurality of sub-bands to obtain a first sub-band mean signal level; and
   determining a first sub-band minimum integration time to obtain the first image frame from the first sub-band mean signal level.

4. The method of claim 1, the method further comprising:
   determining a second sub-band minimum integration time to obtain the at least one second sub-band image frame from the second sub-band mean signal level.

5. The method of claim 1, wherein the image to be displayed is a composite image.

6. The method of claim 1, wherein the image to be displayed is a band ratio image.

7. The method of claim 1, wherein the first sub-band of the plurality of sub-bands comprises at least a portion of an upper short-wave infrared sub-band.

8. The method of claim 1, wherein the second sub-band of the plurality of sub-bands comprises at least a portion of a lower short-wave infrared sub-band.

9. The method of claim 1, the method further comprising:
   when the second sub-band mean signal level is above the second threshold,
   adjusting a focal length of the imaging optics until a threshold signal level has been reached and collecting the at least one second sub-band image frame in the second sub-band,
   wherein the image to be displayed is generated by combining at least two collected frames.

10. The method of claim 9, wherein the focal length of the imaging optics is adjusted until a threshold edge contrast ratio has been reached.

11. The method of claim 9, the method further comprising:
   when the second sub-band mean signal level is above a third threshold,
   collecting at least one image frame in a first portion of the second sub-band; and
   collecting at least one image frame in a second portion of the second sub-band,
   wherein the image to be displayed is generated by combining at least three collected frames.

12. The method of claim 11, wherein the first portion of the second sub-band comprises an upper half of a lower short-wave infrared sub-band.

13. The method of claim 11, wherein the second portion of the second sub-band comprises a lower half of a lower short-wave infrared sub-band.

14. The method of claim 11, the method further comprising:
   sampling the first portion of the second sub-band to obtain a first portion mean signal level;
   determining a first portion minimum integration time to obtain the at least one image frame in the first portion of the second sub-band from the first portion mean signal level;
   sampling the second portion of the second sub-band to obtain a second portion mean signal level; and
   determining a second portion minimum integration time to obtain the at least one image frame in the second portion of the second sub-band from the second portion mean signal level.

15. The method of claim 11, the method further comprising:
   sampling a second spectral band to obtain a second band mean signal level, the second spectral band comprising a second plurality of sub-bands;
   collecting at least one second band image frame in the second spectral band when the second band mean signal level is at or below a fourth threshold or above a fifth threshold, wherein the fifth threshold is higher than the fourth threshold,
   wherein the image to be displayed is generated by combining at least two collected frames.

16. The method of claim 15, the method further comprising:
   determining a second band minimum integration time to obtain the at least one second band image frame from the second band mean signal level.

17. The method of claim 15, the method further comprising:
   when the second band mean signal level is at least above the fourth threshold,
   collecting at least one image frame in a red sub-band of the second plurality of sub-bands;
   collecting at least one image frame in a green sub-band of the second plurality of sub-bands; and
   collecting at least one image frame in a blue sub-band of the second plurality of sub-bands,
   wherein the image to be displayed is generated by combining at least four collected frames.

18. The method of claim 17, the method further comprising:
   sampling the red sub-band of the second plurality of sub-bands to obtain a red sub-band mean signal level;

determining a red sub-band minimum integration time to obtain the at least one image frame in the red sub-band from the red sub-band mean signal level;

sampling the green sub-band of the second plurality of sub-bands to obtain a green sub-band mean signal level;

determining a green sub-band minimum integration time to obtain the at least one image frame in the green sub-band from the green sub-band mean signal level;

sampling the blue sub-band of the second plurality of sub-bands to obtain a blue sub-band mean signal level; and determining a blue sub-band minimum integration time to obtain the at least one image frame in the blue sub-band from the blue sub-band mean signal level.

19. The method of claim 17, the method further comprising:

determining a remaining time of a maximum integration time; and dividing the remaining time into a first time portion, a second time portion and a third time portion, wherein the at least one image frame collected in the red sub-band is collected for the first time portion, the at least one image frame collected in the green sub-band is collected for the second time portion, and the at least one image frame collected in the blue sub-band is collected for the third time portion.

20. The method of claim 17, the method further comprising:

collecting at least one third band image frame in a third spectral band, wherein the image to be displayed is generated by combining at least two collected frames.

21. The method of claim 20, wherein the third spectral band comprises at least a portion of a medium wave infrared band.

22. The method of claim 20, wherein the third spectral band comprises at least a portion of a panchromatic band.

23. An imaging system for providing images of a scene comprising:

at least one focal plane for receiving radiation from the scene;

a spectral detector configured to transmit portions of a first spectral band to the at least one focal plane, wherein the first spectral band comprises a first plurality of sub-bands;

an adaptive controller configured to sample the first spectral band to obtain a first band mean signal level, collect at least one first band image frame in the first spectral band when the first band mean signal level is at or below the first threshold, collect at least one first sub-band image frame in a first sub-band of the plurality of sub-bands when the first band mean signal level is above the first threshold, sample a second sub-band of the first plurality of sub-bands to obtain a second sub-band mean signal level, and collect at least one second sub-band image frame in the second sub-band when the second sub-band mean signal level is at or below a second threshold; and a data combiner configured to combine at least two collected frames to generate an image to be displayed.

24. The imaging system of claim 23, wherein the adaptive controller is further configured to adjust a focal length of the image optics until a threshold signal level has been reached, and collect the at least one second sub-band image frame in the second sub-band, when the second sub-band mean signal level is above the second threshold, wherein the data combiner is further configured to combine at least two collected frames to generate the image to be displayed.

25. The imaging system of claim 23, wherein the adaptive controller is further configured to adjust a focal length of the image optics until a threshold edge contrast ratio has been reached, and collect the at least one second sub-band image frame in the second sub-band, when the second sub-band mean signal level is above the second threshold, wherein the data combiner is further configured to combine at least two collected frames to generate the image to be displayed.

26. The imaging system of claim 24, wherein the adaptive controller is further configured to collect at least one image frame in a first portion of the second sub-band and collect at least one image frame in a second portion of the second sub-band, when the second sub-band mean signal level is above a third threshold, wherein the data combiner is further configured to combine at least three collected frames to generate the image to be displayed.

27. The imaging system of claim 26, wherein the adaptive controller is further configured to sample a second spectral band to obtain a second band mean signal level, the second spectral band comprising a second plurality of sub-bands, and collect at least one second band image frame in the second spectral band when the second band mean signal level is at or below a fourth threshold or above a fifth threshold, wherein the fifth threshold is higher than the fourth threshold, and wherein the data combiner is further configured to combine at least two collected frames to generate the image to be displayed.

28. The imaging system of claim 7, wherein the adaptive controller is further configured to collect at least one red sub-band image frame in a red sub-band of the second plurality of sub-bands for the first time portion, collect at least one green sub-band image frame in a green sub-band of the second plurality of sub-bands for the second time portion, and collect at least one blue sub-band image frame in a blue sub-band of the second plurality of sub-bands for the third time portion, when the second band mean signal level is at least above the fourth threshold, wherein the image to be displayed is generated by combining at least four collected frames.

29. The imaging system of claim 28, wherein the adaptive controller is further configured to divide a remaining time of a maximum integration time into a first time portion, a second time portion, and a third time portion, and wherein the at least one red sub-band image frame is collected for the first time portion, the at least one green sub-band image frame is collected for the second time portion, and the at least one blue sub-band image frame is collected for the third time portion.

30. A method of obtaining imagery of ambient temperature objects at nighttime, the method comprising:

receiving radiation from a scene impinging on at least one focal plane;

sampling an upper short wave infrared band of a first band to obtain an upper short wave infrared mean signal level;

determining an upper short wave infrared band minimum integration time to obtain an upper short wave infrared frame from the upper short wave infrared mean signal level;

collecting the upper short wave infrared frame for the upper short wave infrared band minimum integration time; and generating an image to be displayed from the upper short wave infrared frame.

31. The method of claim 30, the method further comprising:

sampling the first band to obtain a first band mean signal level;
when the first band mean signal level is below a first threshold,
> sampling a lower short wave infrared band of the first band to obtain a lower short wave infrared mean signal level;
> determining a lower short wave infrared band minimum integration time to obtain a lower short wave infrared frame from the lower short wave infrared mean signal level;
> collecting the lower short wave infrared frame for the lower short wave infrared band minimum integration time;

when the first band mean signal level is above the first threshold,
> sampling a lower short wave infrared band of the first band to obtain a lower short wave infrared mean signal level;
> determining a lower short wave infrared band minimum integration time to obtain a lower short wave infrared frame from the lower short wave infrared mean signal level;
> collecting the lower short wave infrared frame for the lower short wave infrared band minimum integration time; and combining at least two frames to generate the image to be displayed.

32. The method of claim 31, the method further comprising:
> collecting a medium wave infrared frame in a medium wave infrared band.

33. The method of claim 32, the method further comprising:
> collecting a panchromatic frame in a panchromatic band.

* * * * *